United States Patent
Domenig et al.

(10) Patent No.: US 9,024,277 B2
(45) Date of Patent: May 5, 2015

(54) SYSTEMS METHODS AND DEVICES FOR DISINFECTING USING UV LIGHT

(71) Applicants: Georg Domenig, Kernersville, NC (US); Caroline Domenig, Kernersville, NC (US)

(72) Inventors: Georg Domenig, Kernersville, NC (US); Caroline Domenig, Kernersville, NC (US)

(*) Notice: Subject to any disclaimer, the term of this patent is extended or adjusted under 35 U.S.C. 154(b) by 0 days.

(21) Appl. No.: 14/499,665

(22) Filed: Sep. 29, 2014

(65) Prior Publication Data

US 2015/0069266 A1    Mar. 12, 2015

Related U.S. Application Data

(63) Continuation of application No. 13/769,301, filed on Feb. 16, 2013, now Pat. No. 8,847,174.

(60) Provisional application No. 61/599,840, filed on Feb. 16, 2012.

(51) Int. Cl.
| | |
|---|---|
| *G01N 23/00* | (2006.01) |
| *A61L 2/24* | (2006.01) |
| *A61L 2/10* | (2006.01) |
| *G02B 5/02* | (2006.01) |

(52) U.S. Cl.
CPC ... *A61L 2/24* (2013.01); *A61L 2/10* (2013.01); *G02B 5/0278* (2013.01)

(58) Field of Classification Search
CPC ........ A61L 2/10; A61L 2202/122; A61L 9/20
USPC ............................ 250/453.11–455.11, 504 R
See application file for complete search history.

(56) References Cited

U.S. PATENT DOCUMENTS

| | | | | |
|---|---|---|---|---|
| 5,620,622 | A | * | 4/1997 | Lang .............................. 219/385 |
| 2003/0034459 | A1 | * | 2/2003 | Bonin ......................... 250/491.1 |

* cited by examiner

*Primary Examiner* — Michael Maskell

(57) ABSTRACT

An apparatus includes an enclosure including one or more ultraviolet lights configured to kill germs, the enclosure including a drawer for placing items into and removing items from the enclosure, wherein the enclosure is configured for insertion into an existing cabinet. The apparatus can include an adjustable width bracket, wherein the adjustable width bracket allows the enclosure to be secured against side surfaces within the existing cabinet. The apparatus can also include an adjustable depth bracket, wherein the adjustable depth bracket allows the enclosure to be secured against a back surface within the existing cabinet. The apparatus can also include a bottom bracket, wherein the bottom bracket allows the enclosure to be secured against a bottom surface of the existing surface. In one example, the enclosure is connected to an air filtration system.

6 Claims, 19 Drawing Sheets

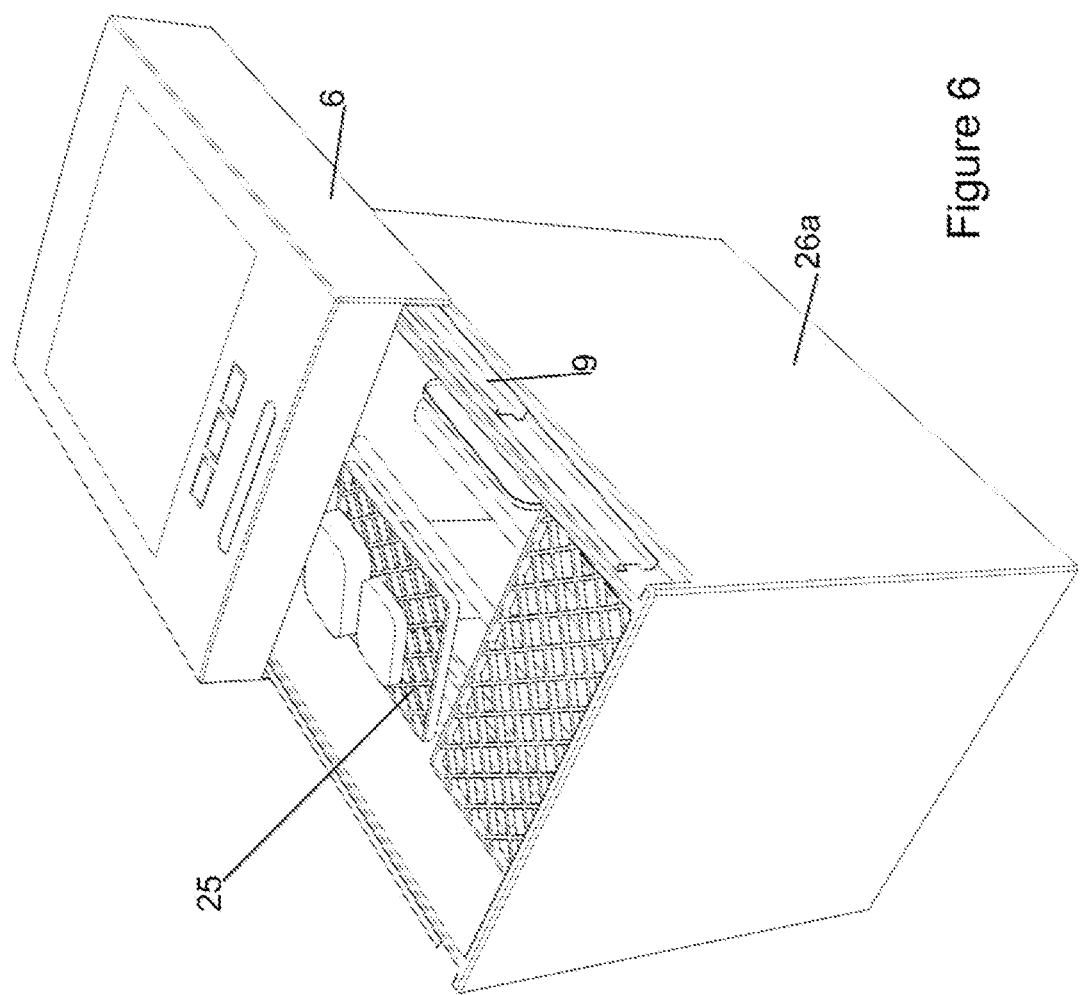

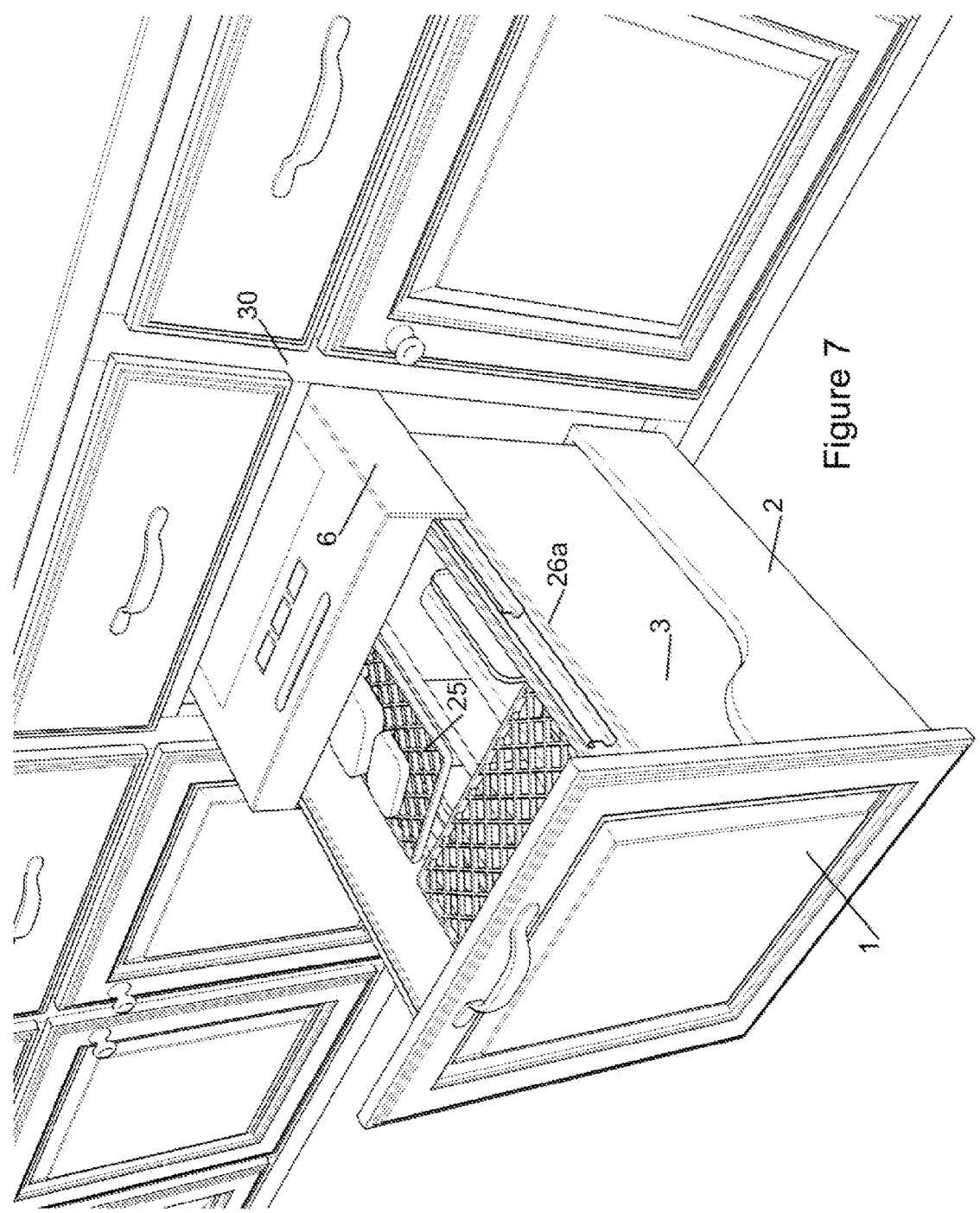

SYSTEMS METHODS AND DEVICES FOR DISINFECTING USING UV LIGHT

RELATED APPLICATIONS

This application claims priority to U.S. Non-Provisional patent application Ser. No. 13/769,301, filed 16 Feb. 2013, which claims priority to U.S. Provisional Patent Application No. 61/599,840, filed 16 Feb. 2012.

BACKGROUND

1. Technical Field

The present disclosure relates to disinfection by UV light technology.

2. Introduction

Germs in the home, especially the kitchen and bathroom, are prevalent even with diligent attempts to keep the home clean. According to an article by Dr. Joseph Mercolal on Mercola.com, "Despite good efforts by most to keep their homes germ free over 65% of colds, 50% of all cases of diarrhea and 50% to 80% of food-borne illnesses are caught in the home, and common household items are often to blame." There are more than 250 known food-borne diseases, according to Rich Maloof2 (MSN Health & Fitness) and include botulism, *listeria*, hepatitis A, *salmonella* and *E-Coli*. The most germ-laden room in the home is the kitchen, the germiest items are the sponge, wash rags/cloths, dishtowels, and the germiest spot is the kitchen sink (not the toilet).

Sponges, rags and towels have a damp environment, which allows bacteria to thrive. "Bacteria colonies with a total population exceeding 50 million" can live on what you use to wipe or dry dishware, silverware, cookware, countertops, sinks, bathtubs, etc.

Cracks and knife cuts in cutting boards, plastic or wood, can provide hiding places for bacteria to grow. It gets complicated when wooden chopping blocks are supposed to be sanded when they get crevices or when people are supposed to use different boards for meat and vegetables/fruits and breads, etc.

Simple washing cannot eliminate the germs on fresh fruits and vegetables. IDEXX Labs, a diagnostic testing service in Westbrook, Main found that 10 out of 39 samples of fresh bean sprouts, all purchased from local grocers had 7,000 *E-Coli* bacteria per gram. The tester, Elizabeth Ehrenfeld, found that "washing the sprouts did not drop the bacterial counts very much." The Food Drug Administration inspects less than 2 percent of nonmeat imports and the GAO reports the FDA "cannot be relied upon to keep pathogen-tainted products out of the US food supply.

Trash/waste/recycling is full of germs and bacteria; as a result, waste/trash and recycling bins can smell bad. Killing the bacteria can help reduce or eliminate odors. An air circulation mechanism used together with the UV lights, can also help reduce or eliminate odors.

Ultraviolet lights, which have been used for quite some time in hospital to disinfect surfaces, have not been available for kitchen and bath cabinet usage. The UV lights used in the disclosed technology can emit UV-A, UV-B and UV-C lights; within the set time of exposure to the germicidal effects of the UV lights, 99% of the targeted germs, bacteria and viruses are destroyed. The UV lights mounted within the cabinet, drawer, pullout, rollout tray, tip-out tray, self-standing unit, or portable unit sterilizes the items exposed. Although the drawings are kitchen oriented, the invention is not limited to kitchen use and can be applied to bathrooms, offices, etc. Each embodiment can include reflective/mirror lining, which reflects the UV lights.

The ultraviolet lights are located in the cabinets, drawers, pullouts and tip-out sink trays with a timer/control circuit that activates the UV lights for a set length of time and then shuts them off. A safety switch allows the UV lights to burn only when the unit (cabinet, drawer, pullout, sink tray) is closed. The disclosed technology is designed to fit into the kitchen and bath cabinet manufacturers and office furniture standard sizes.

Disposable batteries, rechargeable batteries or electric current or solar-based energy can power the UV light. The timer will be programmable (from 5 seconds and up) depending on the item(s) to be disinfected. The UV lights are equipped with a parabolic light diffuser (screen/grate) that directs the light to the desired surfaces and/or items. A safety switch (8) is included on each embodiment (but can be located in various places) and prevents the UV light(s) from functioning unless the unit is closed.

A system that suctions the air within the disinfecting filter and emits sanitized air can be used in conjunction with the UV light system described above. The air circulation system may or may not heat the air, in addition to cleaning it.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are systems, methods, and devices for disinfecting consumer items using UV light.

In accordance with the disclosed technology, disinfection of items such as sponges, towels, trash, cutting boards, is possible in the home and office by integrating disinfecting UV light(s) and/or air circulation mechanism into cabinets, drawers, rollout trays, pullouts, tip-out sink trays, etc. The light(s) are fully concealed when they are in operation. The disclosed is designed to fit industry standard sizes for kitchen and bath cabinet manufacturers, as well as furniture and office furniture manufacturers. The disclosed technology enables existing manufacturers to insert the disclosed technology easily and efficiently. Furthermore, consumers can install the disclosed technology into their preexisting cabinets, drawers, rollout trays, pullouts, tip-out sink trays, etc. easily and quickly. Also, one embodiment of the disclosed technology allows for easy shipping by its RTA (Ready to Assemble) design. Furthermore, the disclosed technology makes the production of the UV light technology efficient and cost effective.

BRIEF DESCRIPTION OF THE DRAWINGS

In order to describe the manner in which the above recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are

FIG. 6 is an exploded view of a drawer box unit, whose bottom section is molded from one piece;

FIG. 7 is an exploded view of a drawer box unit, whose bottom section is molded from one piece installed in a pullout/drawer box;

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

The present disclosure addresses the need in the art for disinfecting items using UV light and/or air circulation mechanism, particular consumer grade goods. A system, method and device are disclosed which disinfect using UV light technology and/or air circulation mechanism and are easily incorporated into existing environments.

Reference will now be made in detail to embodiments of the disclosed technology, one or more examples of which are illustrated in the accompanying attachments. Each example is provided by way of explanation of the disclosed technology, not as a limitation of the disclosed technologies. It will be apparent to those skilled in the art that various modifications and variations can be made in the present invention without departing from the scope or spirit of the invention. For example, features illustrated or described as part of one embodiment can be used on another embodiment to yield a still further embodiment. Thus, it is intended that the present invention cover such modifications and variations that come within the scope of the invention. Thus, it is intended that the present invention cover such modifications and variations that come within the scope of the invention.

While an example embodiment of the disclosed technology deals with kitchen cabinets as a typical application, it is to be understood that the disclosed technology is applicable to any bathroom cabinets, office cabinet, storage cabinets, drawers, pullouts, rollouts, tip-out trays, or swing storage units.

Figure 1:
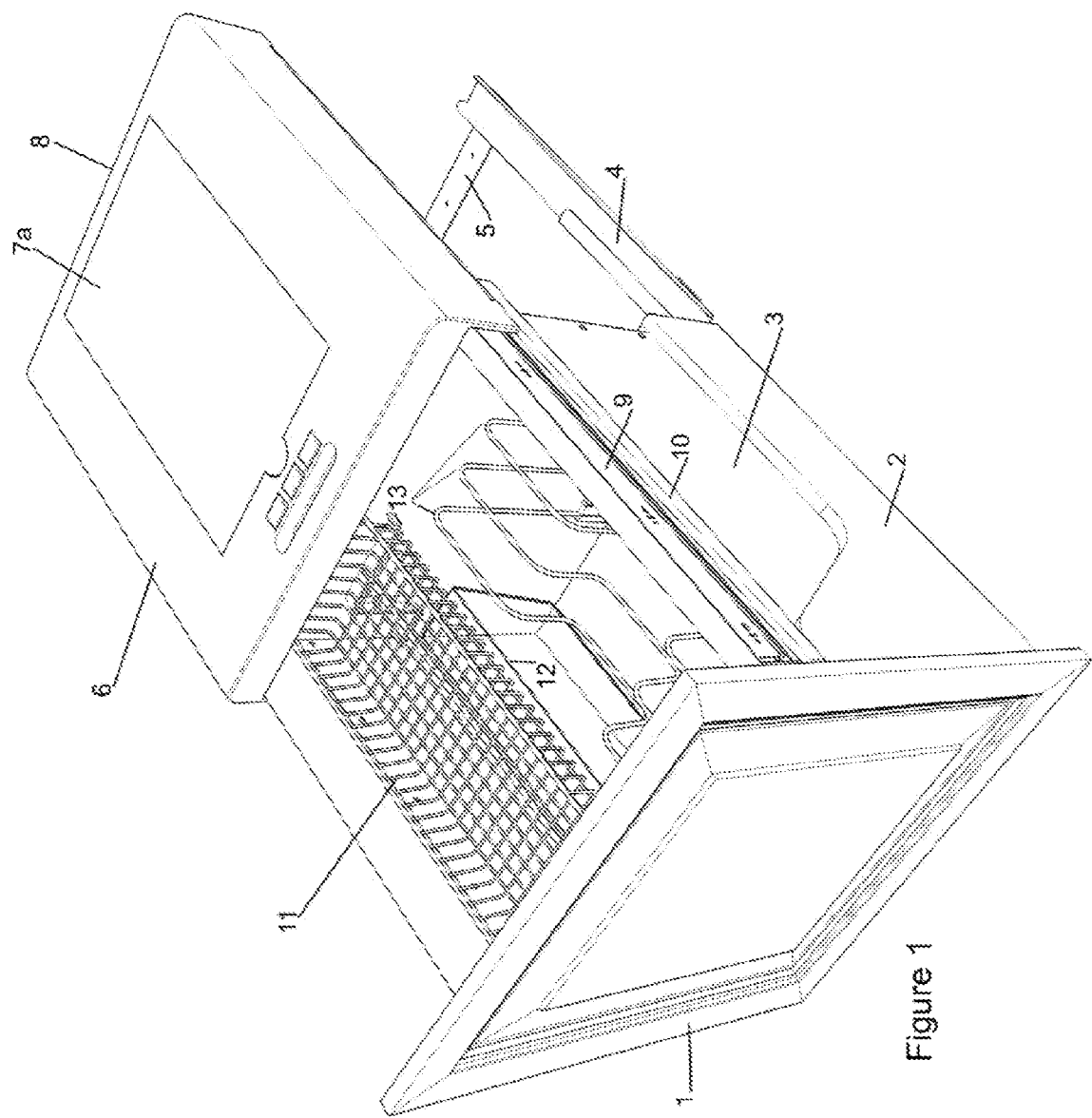
FIG. 1 is an exploded view of a drawer that has an insert unit with the UV light(s) and/or air circulation mechanism that is located within the drawer and has a sliding lid.

FIG. 1 shows a unit (3) that can be placed on an existing pullout/rollout or drawer (1,2). The unit is built with various components, such as a rack (12) to hold a sponge, brush, and other items and chopping block dividers (13), as well as a section to hold produce and other foods, being sanitized by the unit prior to the food being cut, prepared and eaten (11). The sliding lid (6) with pullout slides (9) on mounting supports (10), a cover (7a) and a safety switch (8). The safety switch (8) allows the UV light(s) and/or air circulation mechanism to operate only when the lid (6) is closed. The drawer box unit (1, 2) is mounted on concealed side mounted full extension drawer slides/pullouts (4,5). Features that can be used in conjunction with this drop-in sanitizing unit (but are not required) are side mounted drawer/pullout slides, concealed undermount drawer/pullout slides, mechanical and electrical touch latch system, electric touch open system, touch close system and standard open with soft close systems. The sliding lid (6) is equipped with a timer switch, an on-off switch and a safety lock. Disposable batteries, rechargeable batteries, electricity or solar power can power the unit.

Figure 2:
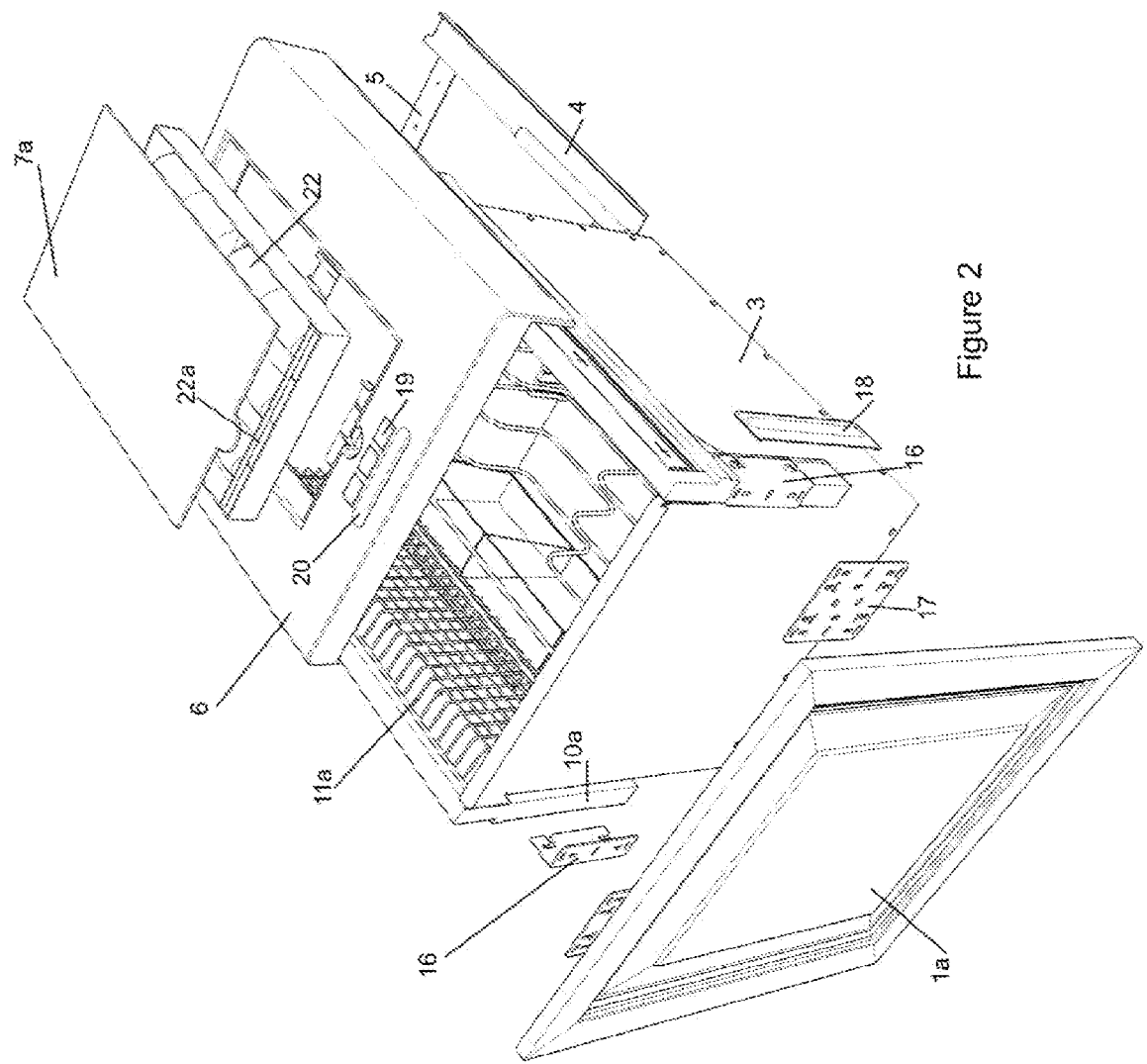
FIG. 2 is an exploded view of the components of a drawer box unit, where the drawer and door fronts are attached or unattached.

FIG. 2 is a self-contained unit (3) that can be installed into a cabinet without a drawer box. The self-contained unit (3) can be mounted directly on side-mount, bottom-mount full-extension slides (4,5) (ball-bearing and non ball-bearing). The finish or material on the unit (self-contained box, drawer, flip-out) is made of antimicrobial material. If a door (1a) attachment is desired, special front brackets (16, 17) are available. These brackets (16, 17) allow height-, side- and in and out adjustments and are available for varying door widths. If there is a special situation where the self-contained unit cannot reach the door rail, extendable door mount brackets (17) solve this issue without need for sub-door panels. Brackets (16, 17) are attached to molding (10a). Once the installment is complete, cover caps (18) cover the screw heads. The foldable adjustable rack (11a) gives access to space below. The sliding lid (6) has a slot/handle (20) for easy opening and closing of the lid. The buttons to control the UV light(s) and/or air circulation mechanism and timer (19) are located on the sliding lid (6). A holder (22) holds the UV light(s) in place. The box kit unit (22a) holds the batteries (disposable or rechargeable) and/or electronics and/or electric connections and/or solar unit (22a) and/or air circulation mechanism. The sliding lid has a cover (7a).

Figure 2A:
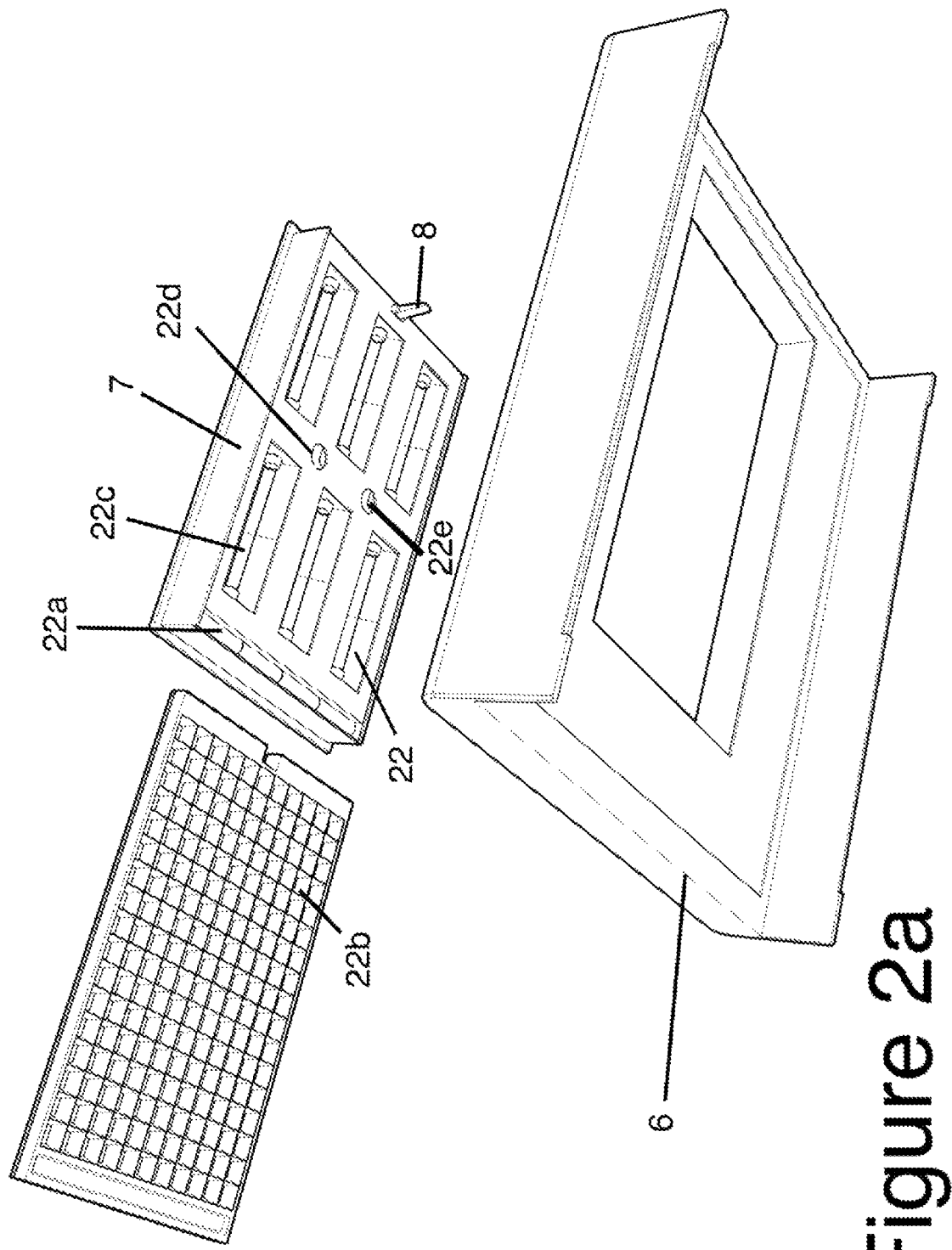
FIG. 2a is a top view of the unit with the ultraviolet (UV) light(s) and/or batteries and/or electronics and/or electric connections and/or solar unit and/or air circulation mechanism and the parabolic screen.

FIG. 2a shows the sliding lid (6) that has a box that holds the UV lights, batteries (disposable or rechargeable) and/or electronics and/or electric connections and/or solar unit (7); the UV lights (22c) are held by the holder (22,22d, 22e). The UV light holder (22) has a reflective surface to bound UV light beams downward. The sliding lid (6) has a parabolic diffuser grate/screen (22*b*).

Figure 3:
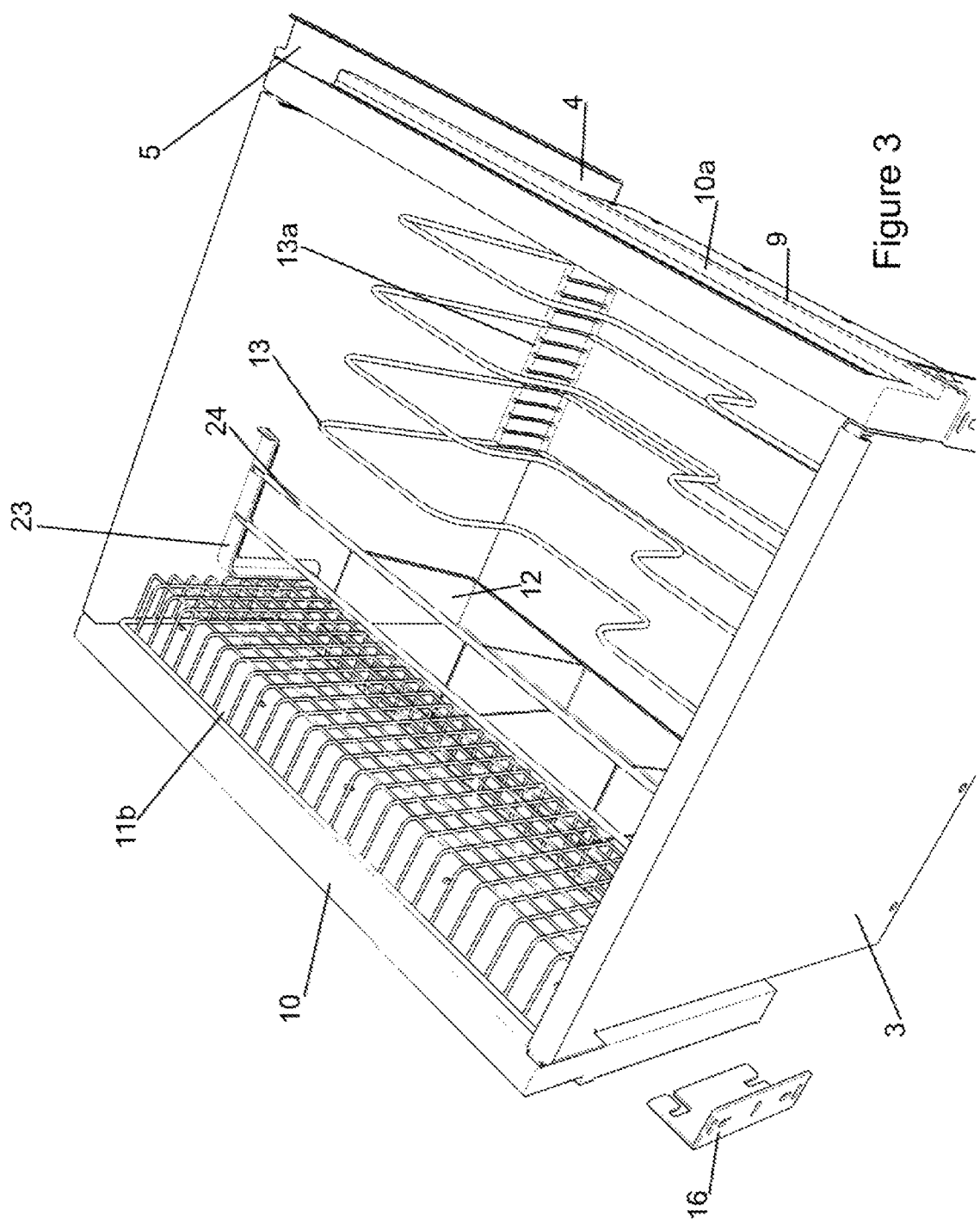
FIG. 3 shows the inside of the layout of the drawer box unit that can hold chopping blocks, towels, sponges, brushes, fruits, vegetables, other items.

FIG. 3 shows the top interior view of the box (3,10), adjustable front bracket for door adjustment (16), the molding (10, 10*a*) to attach the drawer slides (4,5), the foldable rack with the snap system (11*b*) holds the rack in place. The rack support (23) supports the rack in the folded position or unfolded (in use) position. The towel rods (24) are attached to the rack support (23). The chopping block divider(s) (13) are adjustable and can be set in the chopping block divider holder (13*a*). A rack holder (12) holds sponges, brushes and other items to be sanitized.

Figure 4:
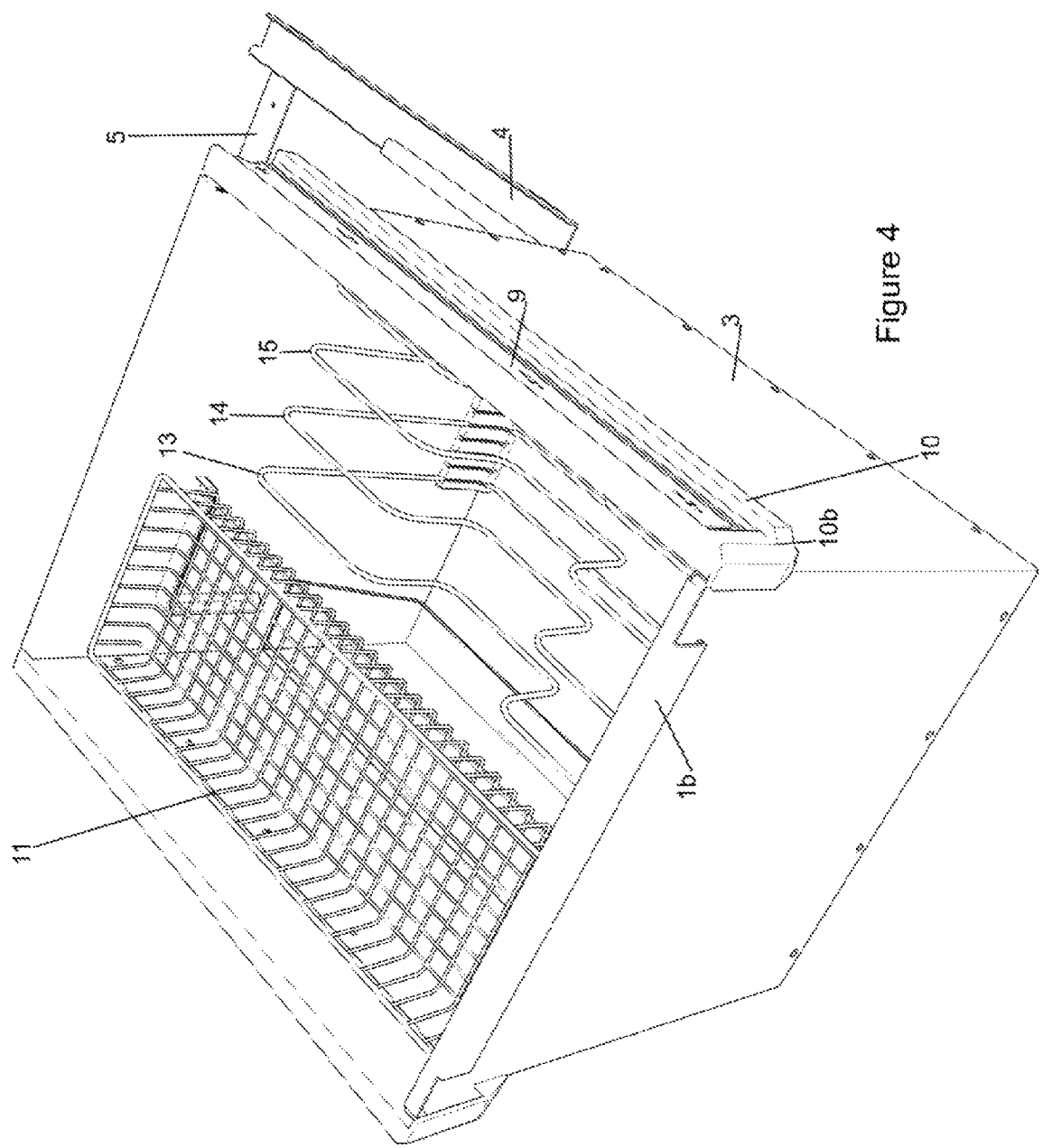
FIG. 4 shows the drawer box/pullout without the drawer/door front. The drawer/door front is attached with hinges to the cabinet.

FIG. 4 shows the top interior view of the box unit (3) and the handle (1*b*). The box (3) is self-contained and can be placed into an existing cabinet. The cabinet door is not attached to the box (1*b*). Therefore, the box (3) is placed in the cabinet on drawer slides (4,5) and then the box unit (3) is opened and closed by utilizing the handle (1*b*). There is a special bevel/angle (10*b*) on the full extension drawer/pullout slides (9) and the molding (10) to attach the drawer/pullout slides. The special bevel/angle (10*b*) prevents the cabinet door from being damaged when the unit is opened and the cabinet door does not open more than 90°. Shown are the adjustable rack (11) and the chopping block dividers (13, 14, 15).

Figure 5:
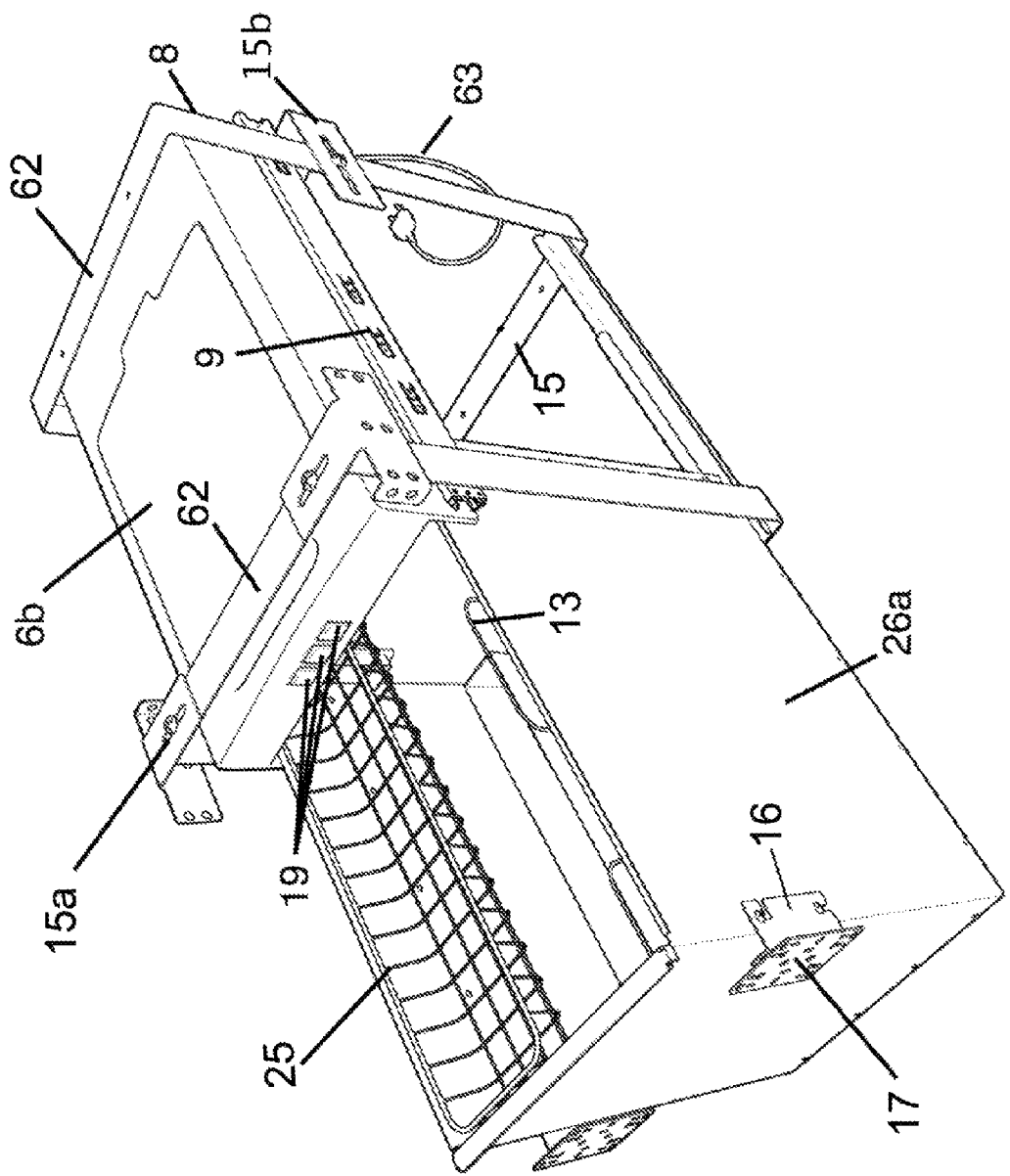
FIG. 5 shows the disclosed technology inserted into a drawer box/pullout and the UV light lid above is pre-attached to the heavy duty frame.

FIG. 5 shows the bottom unit itself (26*a*) with the lid (6*b*) attached to the heavy duty frame (62). Installation is easy. The bottom bracket (15) is mounted to the floor of the cabinet; the upper bracket (15*a*), which is width adjustable, as well as adjustable door mount brackets for overlay doors (16, 17) and/or inset doors is attached to the cabinet face frame. Telescoping back brackets (15*b*) attach to the back wall of the cabinet. The lid is attached to the top of the inside of the frame and has full extension slides (may or may not be ball-bearing), so it can be pulled out to change the filter and/or batteries. For those units powered by electricity, the cord and plug (63) are located on the back of the unit. The cord is automatically refracted by a spring-loaded retraction mechanism to prevent it from becoming tangled when the lid is opened and closed. The foldable rack system (25) allows the user to adjust shelving and storage of items to be sterilized and the chopping block dividers (13) are adjustable as well. Shown are the buttons (19) to control and time the UV light(s) and the safety switch (8) and/or the air circulation mechanism, which insures UV lights and/or air circulation mechanism operate only when the drawer/pullout is closed.

Figure 5A:
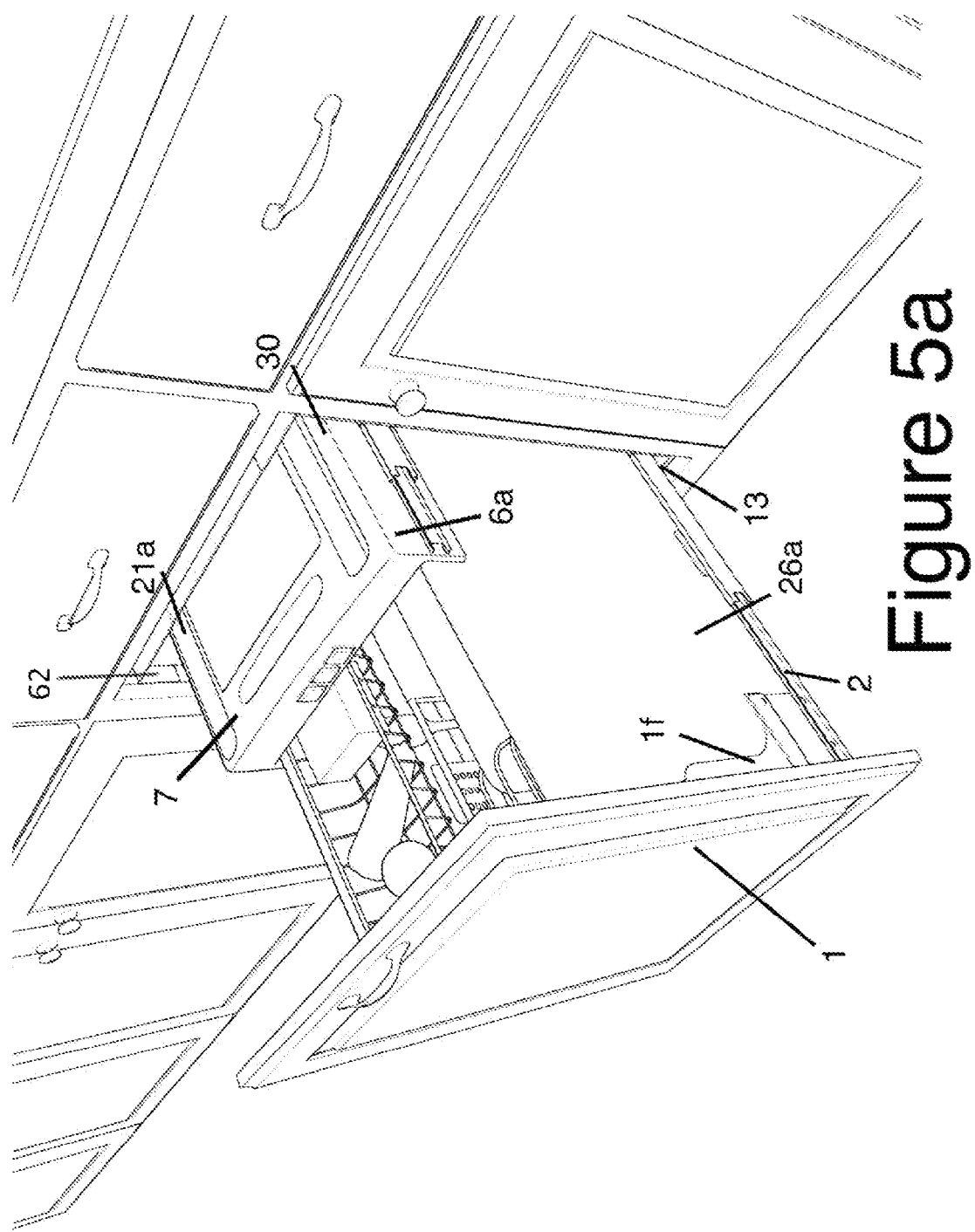
FIG. 5a is an exploded view of a bottom unit (26a) that has the door attached to the unit itself.

FIG. 5*a* shows the bottom unit itself (26*a*) with the attached door (1) on the heavy duty frame (62) on side-mount or bottom-mount full extension slides (2) that goes into the cabinet body (30) attached with build-in adjustable (height, side, in and out) door mount brackets (1*f*). This embodiment has the sliding lid (6*a*) that contains the box that holds the UV light(s), batteries (disposable or rechargeable) and/or electronics and/or electric connections and/or solar unit (7) and/or air circulation mechanism, and has additional dividers (21*a*) for storage, attached with drawer slides and the box unit to the heavy duty frame (62).

Figure 5B:
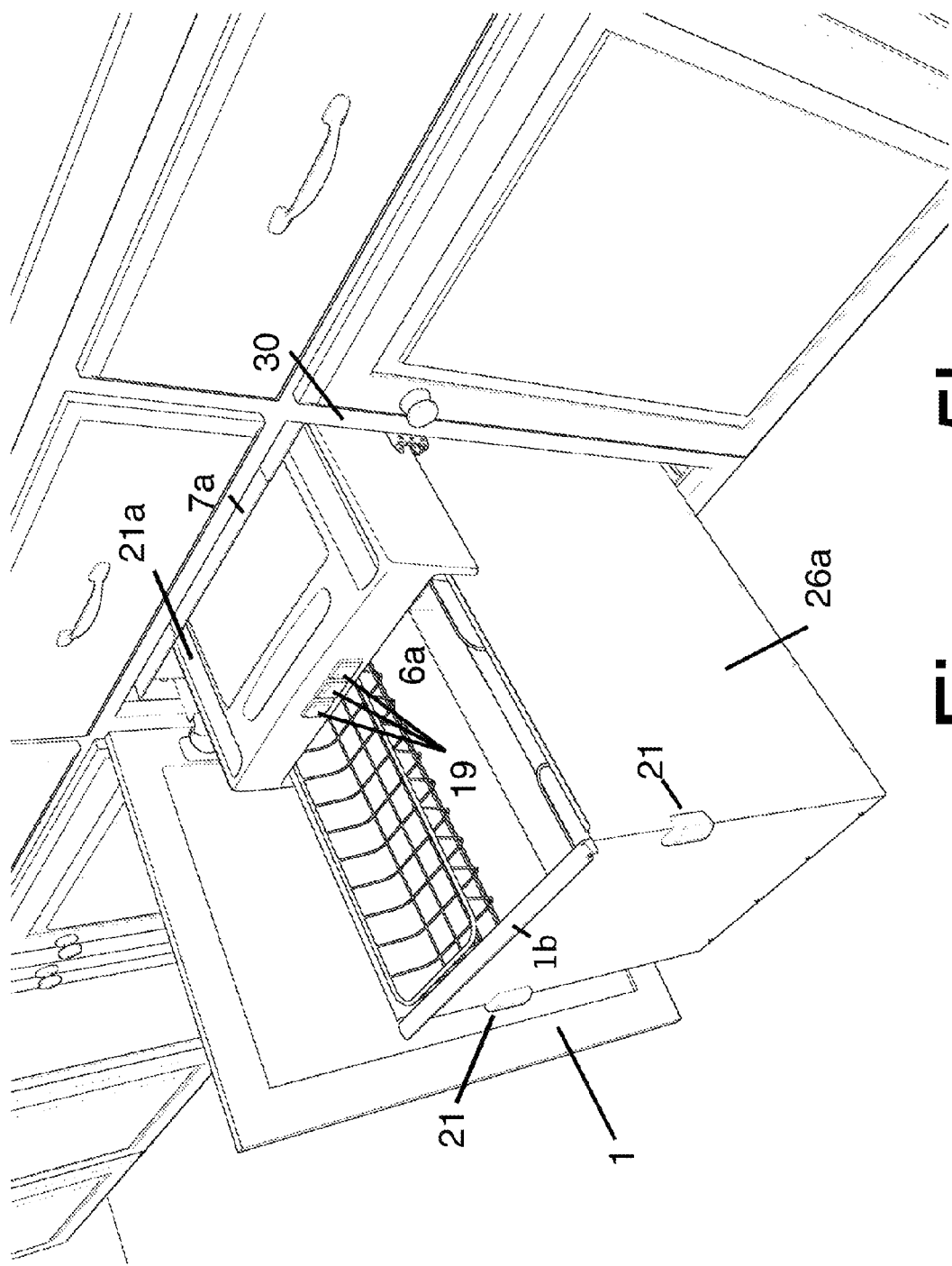
FIG. 5b is an exploded view of a bottom unit (26a) with the door attached to the cabinet body (30)

FIG. 5*b* shows the bottom unit itself (26*a*) with the door (1) attached to the cabinet body (30) by hinges. This requires the same installation as described in paragraph [0045] and FIG. 5*a*. Because the door must be opened to pull out the bottom unit (26*a*), a door protector (21) is mounted on the door-side of the bottom unit (26*a*) to keep the unit (26*a*) from damaging the door (1) and the handle (1*b*) used for pullout out the top unit (6*a*). The sliding lid (6*a*) that holds the ultraviolet (UV) light(s), and/or air circulation mechanism, batteries (disposable or rechargeable) and/or electronics and/or electric connections and/or solar unit, buttons (19), and the cover lid (7*a*) and/or the air circulation mechanism and the other divider(s) (21*a*) give additional storage for items not to be sterilized.

FIG. 6 shows the unit has the bottom piece molded in one-piece (26*a*), full extension slides (9), foldable rack system (25) and a sliding lid (6). A one-piece bottom (26*a*) is more economical to produce.

Figure 6A:
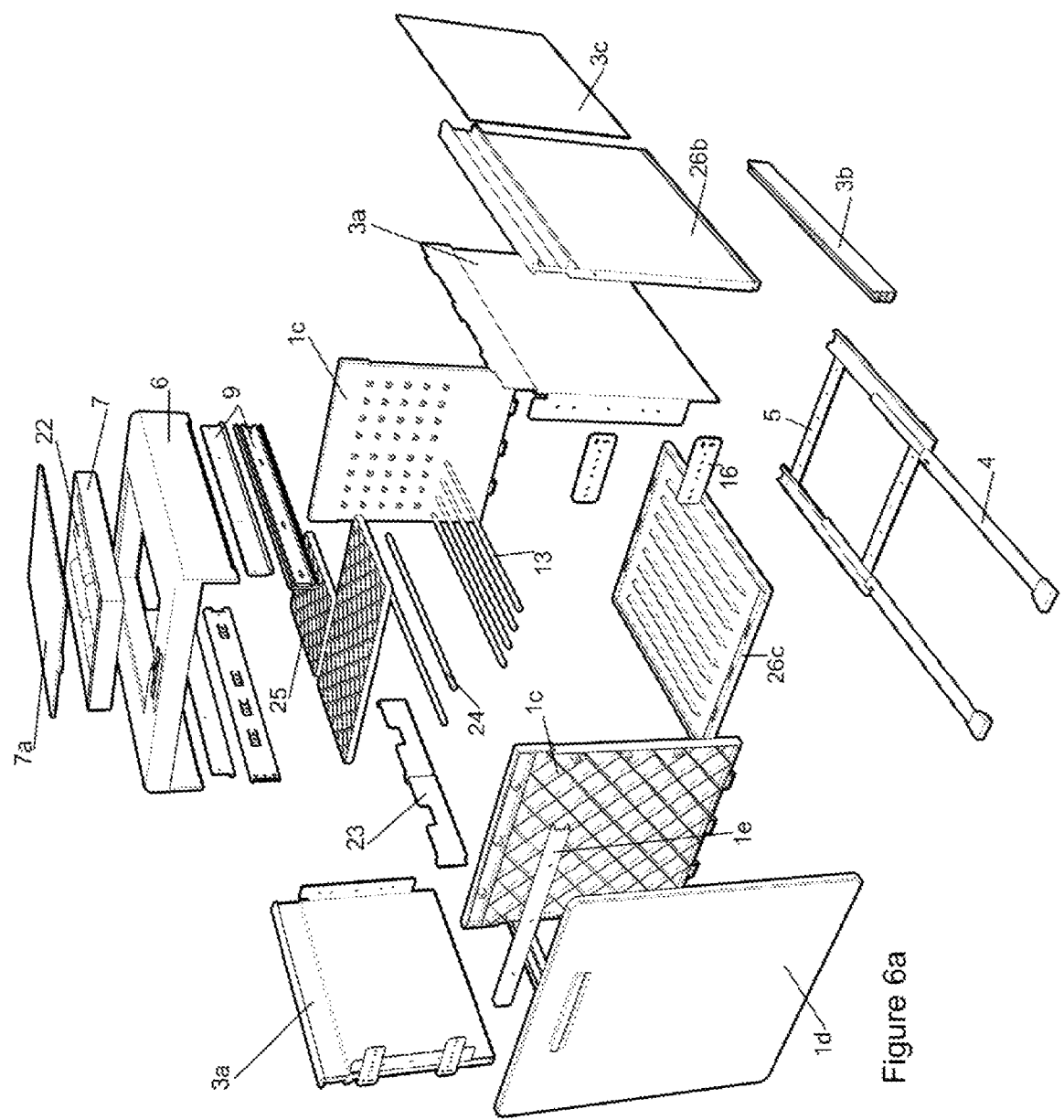
FIG. 6a is an exploded view of drawer box insert unit that is designed for flat pack for easy shipping.

FIG. 6*a* shows the unit is made of parts that are RTA (Ready to Assemble) and can be flat-packed for economical shipping. Parts include the door (1*d*), inside panels (front and back) (1*c*), support bars for strengthening (1*e*), the inside walls of the unit (3*a*), extrusion(s) (3*b*) to capture the side panel(s) (26*b*) and bottom panel(s) (26*c*), outside finished panel(s) (3*c*), drawer slide(s) (4), Drawer slide spacer/attaching bar (5), sliding lid (6), UV light(s) holder (22), the box that contains the UV light(s), batteries (disposable or rechargeable) and/or electronics and/or electric connections and/or solar unit (7) and/or air circulation mechanism, the full-extension drawer slide(s) (9), chopping block divider(s) (13), adjustable front brackets for door adjustment (16), UV light (s) holder (22), rack supports (23), towel rods (24), foldable rack system (25), and panels (26*b*, 26*c*).

FIG. 7 shows the box unit (3) with a one-piece bottom (26*a*) and a door (1) attached to the drawer box (2) installed in a cabinet (30). Inside the box unit (3) is the foldable rack system (25). Also shown is the sliding lid (6) as previously described.

Figure 8:
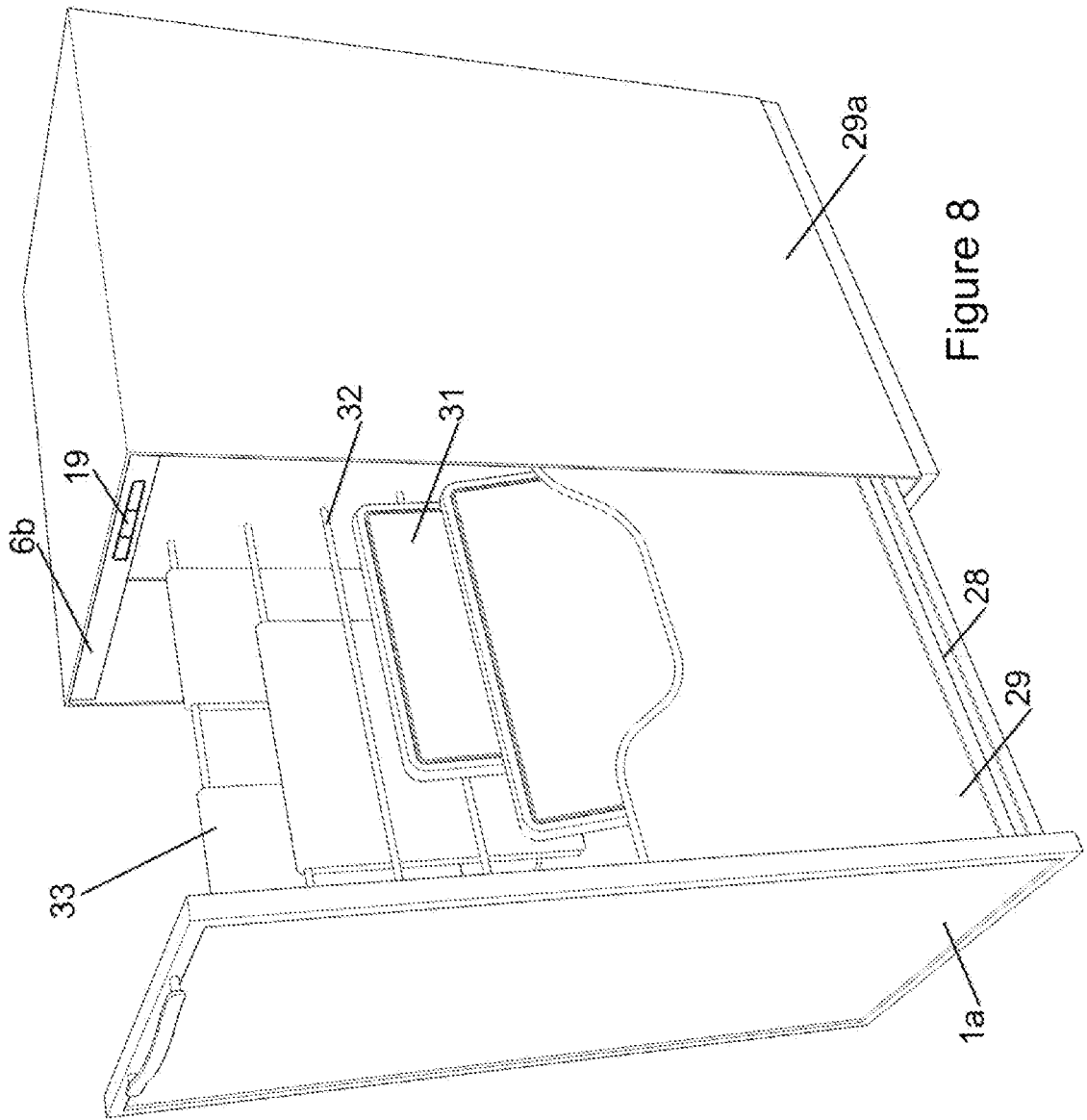
FIG. 8 is a view of a self-contained unit.

FIG. 8 shows a self-contained unit (29*a*) with a door attached with special brackets (1*a*). Shown are the full-extension slides (full extension slides, side-mount or bottom mount, ball-bearing or non ball-bearing) (28), the sliding bar (29) and the chopping block(s) (31), divider bars, towel rack/dowels (32) and towel (33), as well as the lid attached to the top of the inside cabinet (6*b*) and the buttons (19) to control and time UV light(s) and/or air circulation mechanism contained in lid. This embodiment of the disclosed technology can be installed in existing cabinetry (even with narrow spaces) or be self-standing.

Figure 9:
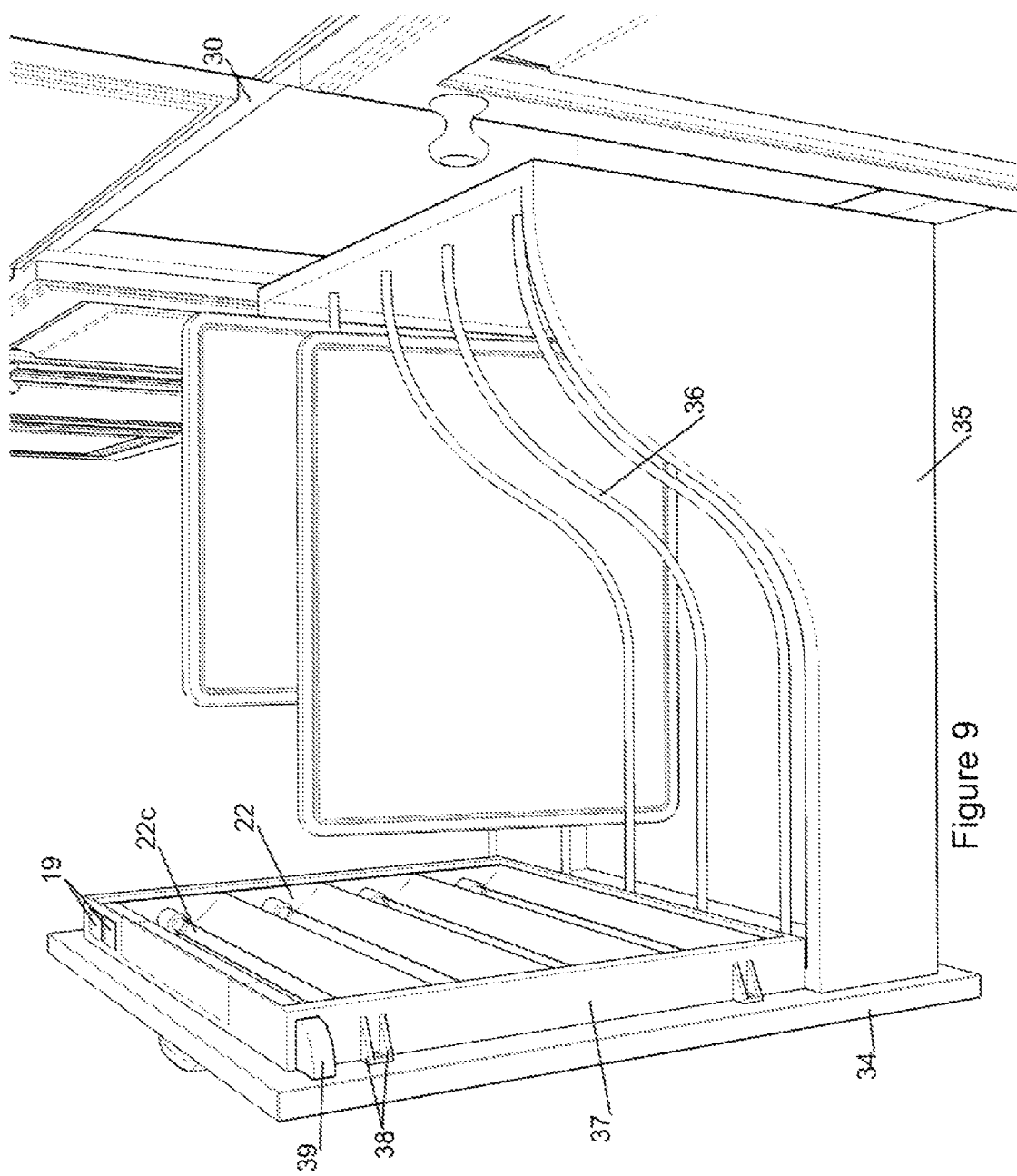
FIG. 9 is a drawer/pullout that shows the UV light attached to the drawer door front.

FIG. 9 shows a drawer box/pullout (35) with the door attached (34) in the cabinet body (30). Also visible are the dividers (36). The UV light box (37) is attached to the drawer front by the adjustable brackets (38). A safety switch (39) ensures the UV light(s) function only when the drawer box unit is closed. As in previous embodiments, there are buttons to control and time UV light(s) (22*c*), the UV light(s) holder (22) and the on/off switch (19).

Figure 10:
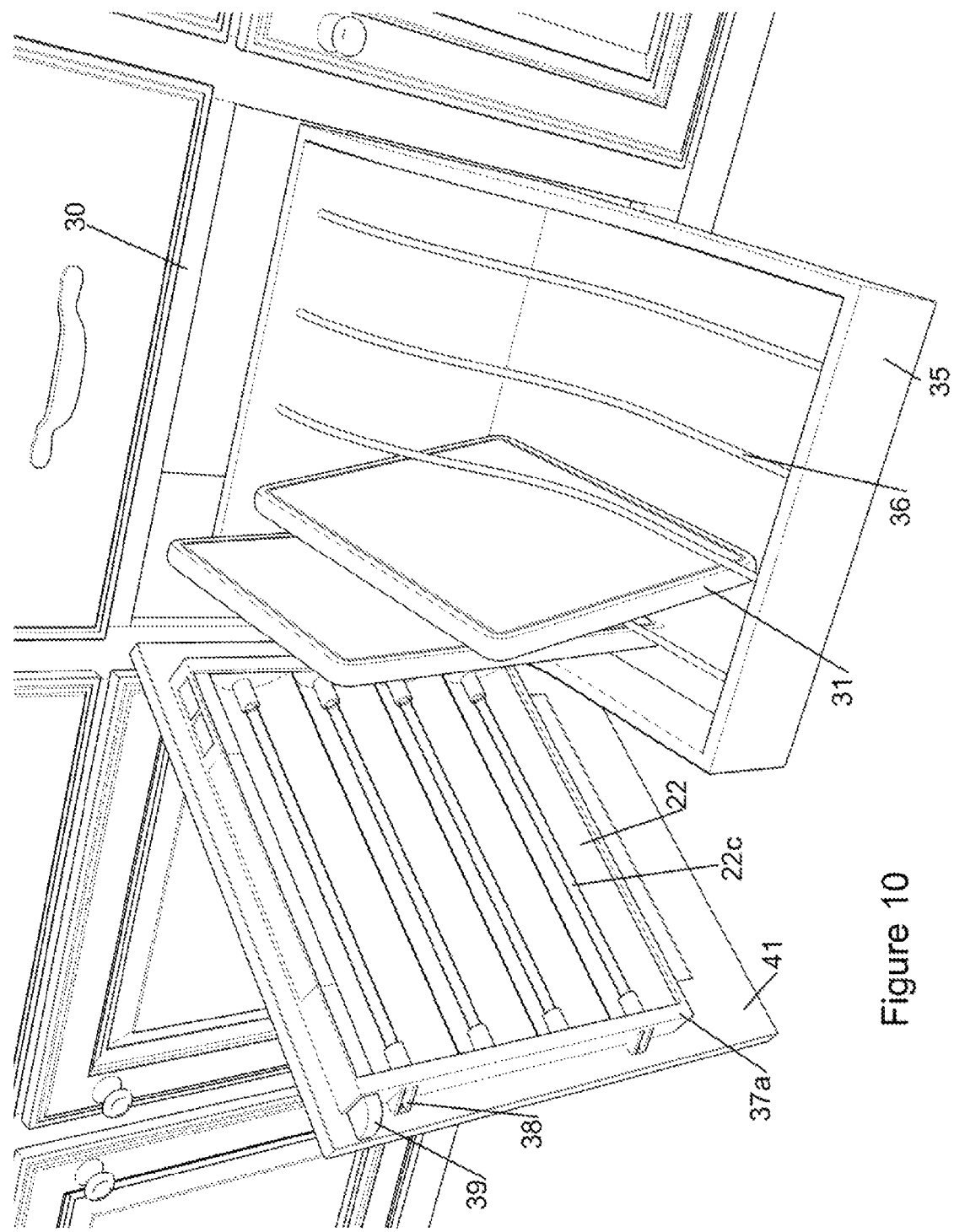
FIG. 10 shows a drawer/pullout and the separate door to which the UV lights are attached.

FIG. 10 shows the embodiment of the pullout/drawer in which the door with hinges (41) is not attached to the drawer box/pullout (35). The view shows the drawer box/pullout (35) in the cabinet body (30), the dividers (36) with the chopping block(s) (31). The UV light box (37*a*) is attached to the inside of the door front (41) by the adjustable brackets (38). A safety switch (39) ensures the UV light(s) function only when the drawer box unit is closed. As in previous embodiments, there are buttons to control and time UV light(s) (22*c*) and the UV light(s) holder (22).

Figure 11:
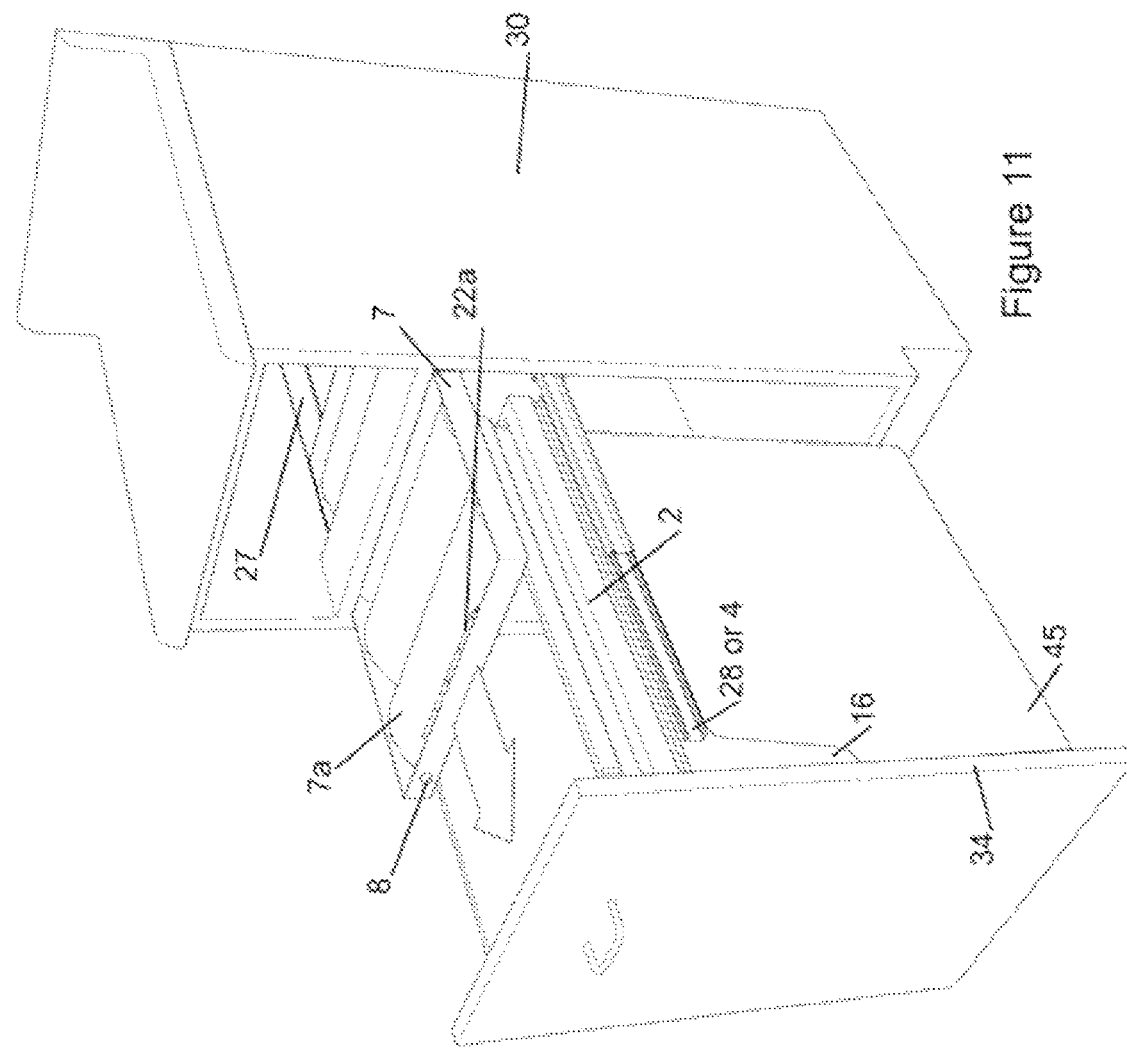
FIG. 11 shows a waste/trash receptacle pullout with the UV light(s) built in the cabinet.

FIG. 11 shows the unit that is designed for the trash receptacle pullout, which can be installed in a cabinet body (30) or be freestanding. Shown are the trash/waste receptacle (45) and the door (34) attached to the drawer/pullout box (2) with special adjustable brackets (16) or hinges. The drawer/pullout box (2) is mounted with side or bottom slides (28,4). A special attachment with drawer slides (27) or screws attached to the inside top of the cabinet, enable the sliding lid cover (7*a*) that holds the box (7) with the UV light(s), and/or air circulation mechanism, batteries (disposable or rechargeable) and/or electronics and/or electric connections and/or solar unit (22a) to move in and out. A safety switch (8) is located on the sliding lid cover (7a).

Figure 12:
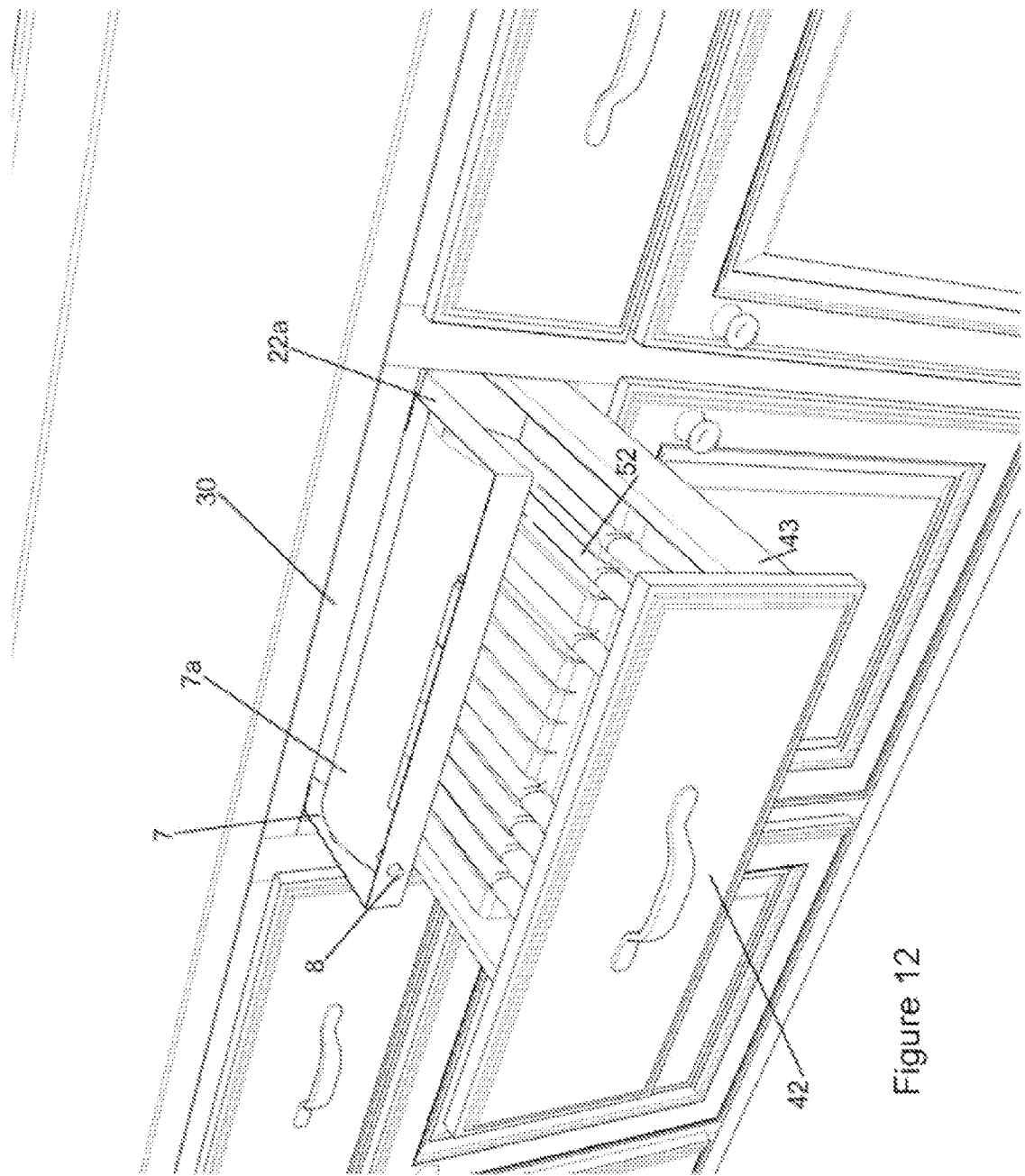
FIG. 12 shows a drawer/pullout within a drawer box to which the UV lights are attached.

FIG. 12 shows a cutlery drawer in a pulled-out position from a cabinet body (30). This embodiment includes all drawers. The drawer front (42) is attached to the drawer box (43), which can contain drawer insert accessories, such as cutlery insert (52). The sliding lid (7a) holds the box (7) with the UV light(s), batteries (disposable or rechargeable) and/or electronics and/or electric connections and/or solar unit (22a) to move in and out. A safety switch (8) is located on the sliding lid (7a).

Figure 13:
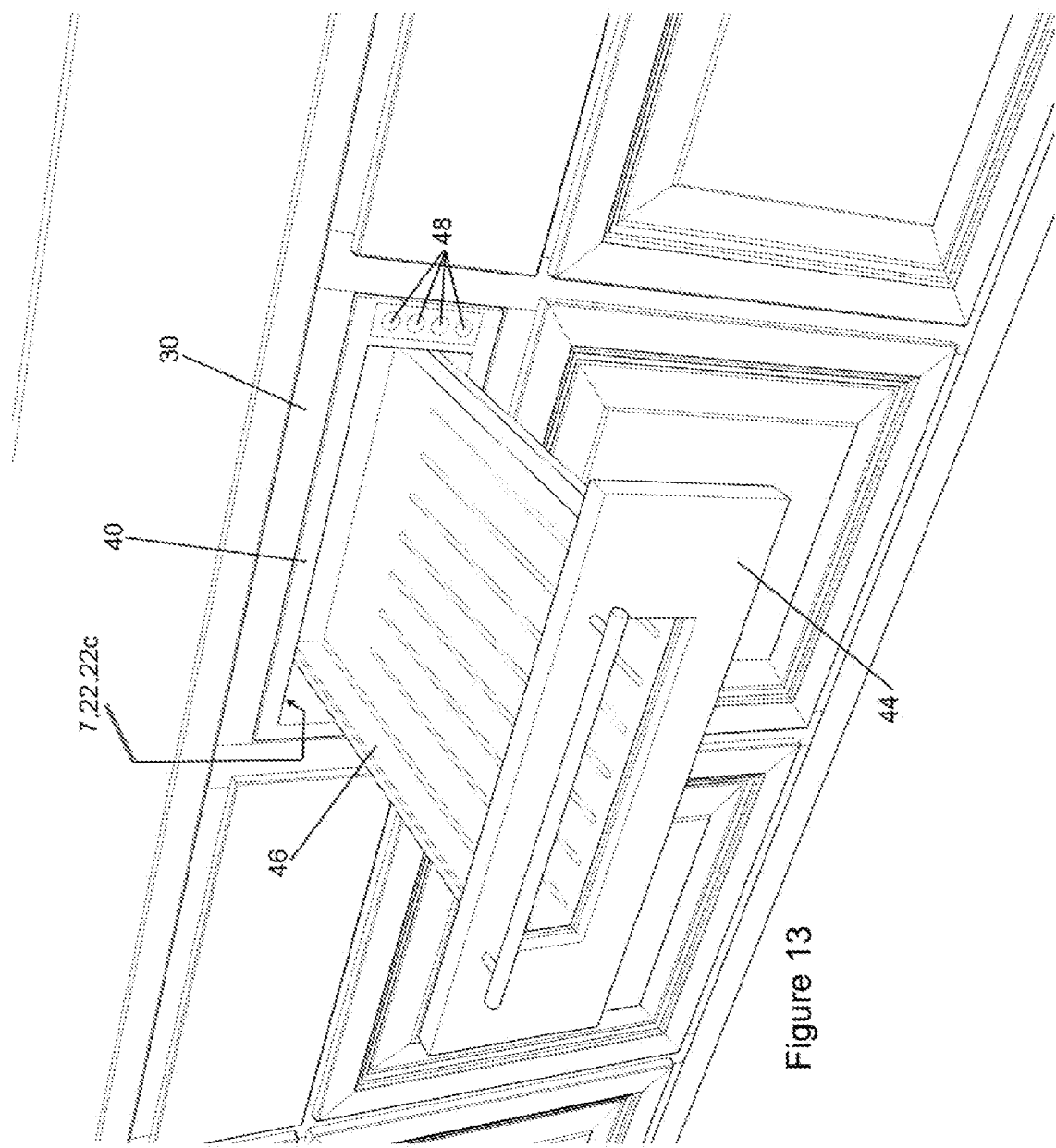
FIG. 13 shows a warmer drawer that also has UV light(s) & kit with batteries (disposable or rechargeable) and/or electronics and/or electric connections and/or solar unit.

FIG. 13 is a warming drawer with integrated UV light(s) sanitizing system. The drawer front (44) is attached to the metal drawer/pullout box (46). Shown is the metal casing (40). The entire system goes into the cabinet body (30). The buttons (48) located on the front control the drawer warmer, UV light(s) and timer. Not visible is the unit (7,22,22c), which is attached underneath the top.

Figure 14:
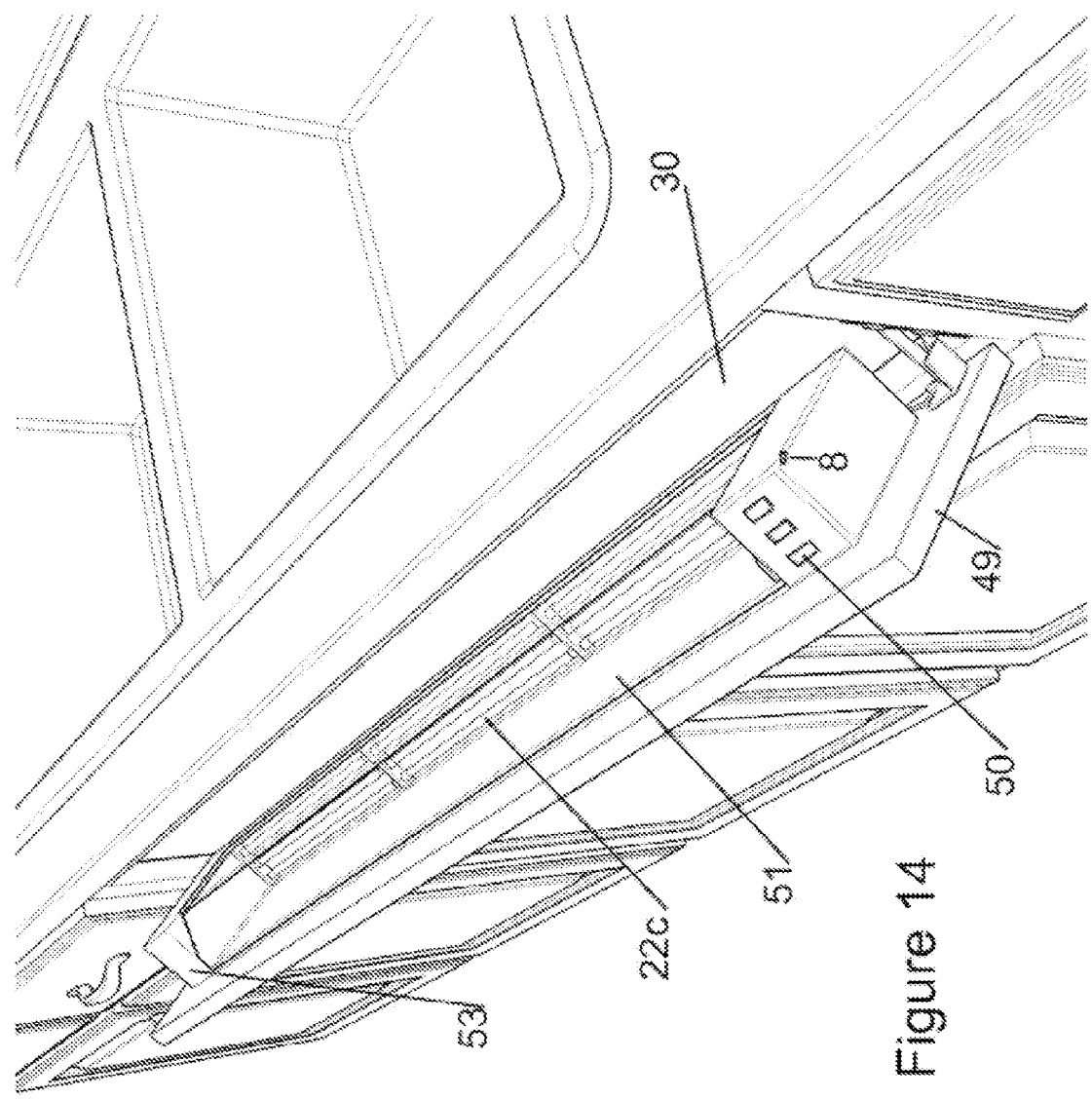
FIG. 14 shows a sink tray storage unit, which the UV lights are attached.

FIG. 14 is a tip-out sink tray box (51) with an attached drawer front (49) and is attached to the cabinet body (30) with special brackets. The tip-out sink tray casing (53) contains the UV light(s), UV light(s) holder, batteries (disposable or rechargeable) and/or electronics and/or electric connections and/or solar unit. Shown are the buttons (50) to control and time UV light(s) (22c), the safety switch (8) and the rack holder for sponge, brush and other similar items.

Figure 15:
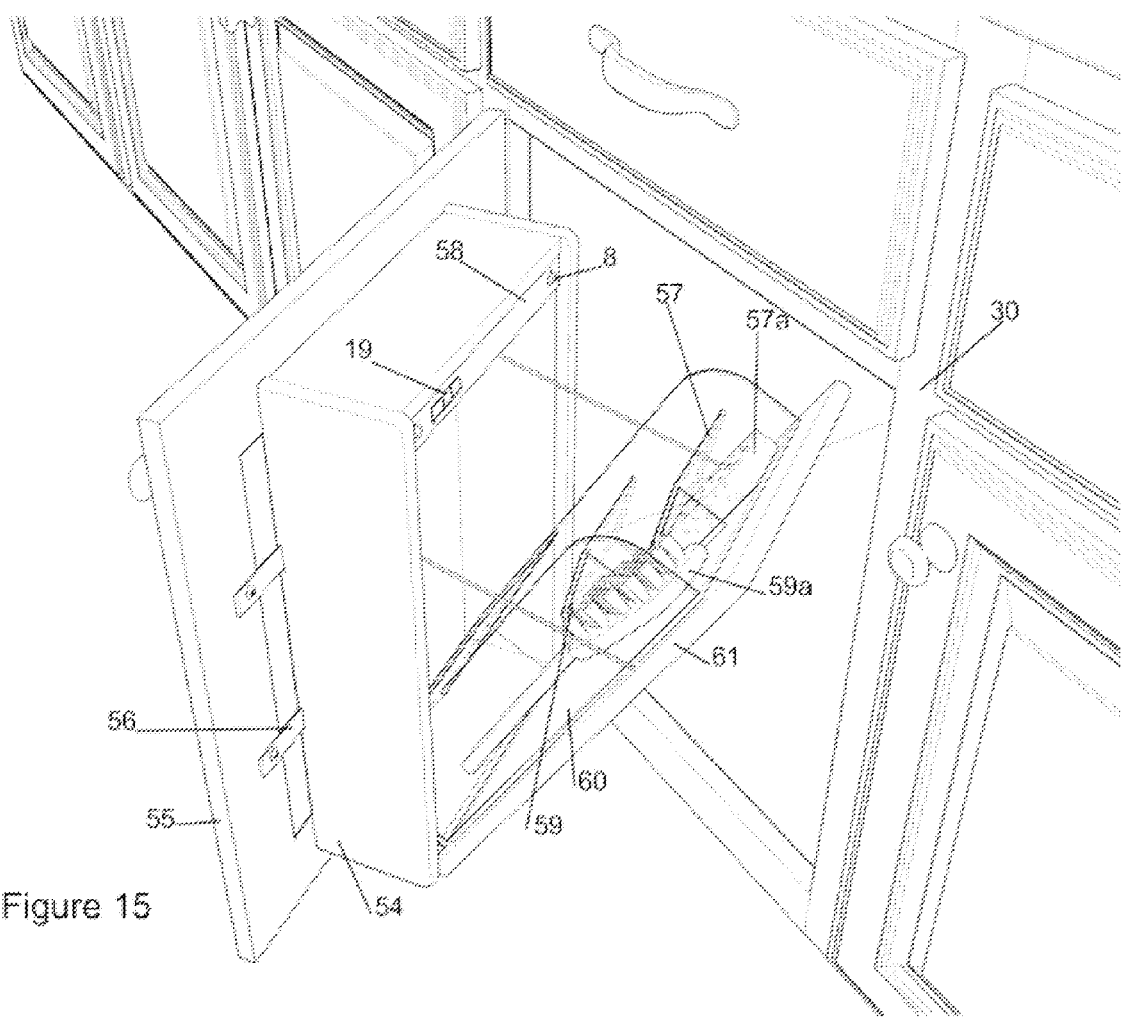
FIG. 15 shows a sink base multi-storage kit that also has UV light(s) & kit with batteries (disposable or rechargeable) and/or electronics and/or electric connections and/or solar unit.

FIG. 15 shows a tip-out storage unit (54) that screws onto the inside of the cabinet door (55) with adjustable bars (56) to adjust for different door sizes. The storage box (54) has a tip-out door (61) that is attached by means of hinge(s). The fixed lid (58) with integrated electronics and UV light(s) and/or batteries (disposable or rechargeable) and/or electronics and/or electric connections and/or solar unit is attached to the upper part of the cabinet (54) on which the buttons (19) to control and time UV light(s) and the safety switch (8) are located. The panel (60) is attached to the front door (61). The brush (59a) is held in the brush holder (59) and the sponge (57a) is held in the sponge holder (57). This does not exclude other items to be sanitized. When the cabinet door (55) is closed, the storage box (54) goes into the cabinet body (30).

The various embodiments described above are provided by way of illustration only and should not be construed to limit the scope of the disclosure. Those skilled in the art will readily recognize various modifications and changes that may be made to the principles described herein without following the example embodiments and applications illustrated and described herein, and without departing from the spirit and scope of the disclosure.

We claim:

1. An apparatus comprising:
    a tip-out enclosure for insertion into an existing cabinet, the tip-out enclosure configured to allow placing items into and removing items from the tip-out enclosure;
    one or more ultraviolet light sources positioned within the tip-out enclosure, the ultraviolet light sources configured to generate ultraviolet light within the tip-out enclosure; and
    a diffuser screen positioned near the ultraviolet light sources to more evenly distribute the generated ultraviolet light within the tip-out enclosure.

2. The apparatus of claim 1, wherein the diffuser screen is a parabolic diffuser screen.

3. The apparatus of claim 1, wherein the tip-out enclosure further includes an adjustable bracket, wherein the adjustable bracket allows the tip-out enclosure to be secured against one or more surfaces within the existing cabinet.

4. The apparatus of claim 1, wherein the tip-out enclosure is connected to an air filtration system, wherein the air filtration system pulls air from the tip-out enclosure, forces the air through a filter, and then pushes filtered air back into the tip-out enclosure.

5. The apparatus of claim 1, wherein the tip-out enclosure further includes an adjustable door mount bracket on the drawer for attaching a kitchen cabinet door to the tip-out enclosure such that the door matches the existing cabinet.

6. The apparatus of claim 1, wherein the tip-out enclosure further includes a timer for controlling how long the ultraviolet lights are active.

\* \* \* \* \*